(12) United States Patent
Lindacher

(10) Patent No.: US 7,559,652 B2
(45) Date of Patent: Jul. 14, 2009

(54) ADAPTIVE OPTIC OPHTHALMIC DESIGN SYSTEM

(75) Inventor: Joseph Michael Lindacher, Suwanee, GA (US)

(73) Assignee: Novartis AG, Basel (CH)

( * ) Notice: Subject to any disclaimer, the term of this patent is extended or adjusted under 35 U.S.C. 154(b) by 135 days.

(21) Appl. No.: 11/643,079

(22) Filed: Dec. 21, 2006

(65) Prior Publication Data

US 2007/0139614 A1 Jun. 21, 2007

Related U.S. Application Data

(60) Provisional application No. 60/752,717, filed on Dec. 21, 2005.

(51) Int. Cl.
*A61B 3/10* (2006.01)
(52) U.S. Cl. .................................. 351/212; 351/205
(58) Field of Classification Search ................. 351/200, 351/205, 210–212, 221
See application file for complete search history.

(56) References Cited

U.S. PATENT DOCUMENTS

| | | | |
|---|---|---|---|
| 4,861,156 A | 8/1989 | Terry | 351/243 |
| 5,777,719 A | 7/1998 | Williams et al. | 351/212 |
| 6,095,651 A | 8/2000 | Williams et al. | 351/246 |
| 6,338,559 B1 | 1/2002 | Williams et al. | 351/212 |
| 6,428,533 B1 | 8/2002 | Bille | 606/11 |
| 6,572,230 B2 | 6/2003 | Levine | 351/221 |
| 6,582,079 B2 | 6/2003 | Levine | 351/221 |
| 6,595,643 B2 | 7/2003 | Levine | 351/221 |
| 6,609,794 B2 | 8/2003 | Levine | 351/221 |
| 7,111,938 B2 | 9/2006 | Andino et al. | 351/212 |
| 7,195,354 B2 | 3/2007 | Olivier et al. | 351/205 |
| 2003/0223037 A1 | 12/2003 | Chernyak | 351/209 |
| 2004/0008323 A1 | 1/2004 | Williams | 351/212 |
| 2004/0100619 A1 | 5/2004 | Olivier et al. | 351/221 |
| 2005/0030474 A1 | 2/2005 | Sumiya | 351/211 |
| 2005/0225725 A1* | 10/2005 | Warden et al. | 351/216 |
| 2006/0023163 A1 | 2/2006 | Foster | 351/246 |
| 2006/0232846 A1 | 10/2006 | Himmer et al. | 359/224 |
| 2006/0238710 A1 | 10/2006 | Dick et al. | 351/211 |

OTHER PUBLICATIONS

Imagine Eyes, Mirao 52-d Deformable Membrane Mirror, 2005, 1 page.
Imagine Eyes, Mirao 52-d Deformable Membrane Mirror, Adaptive Optics Adapted to Eyecare, 2006, 1 page.
Olivier et al., "Eyes Can See Clearly Now," Science & Technology Review, 2003, pp. 12 and 13.
Prieto et al., "Adaptive Optics with a Programmable Phase Modulator: Applications in the Human Eye," Optics Express, 2004, vol. 12, pp. 4059-4071.
R & D Magazine, "Vision Correction in the 21st Century," 2006, 1 page.

* cited by examiner

*Primary Examiner*—Scott J Sugarman
*Assistant Examiner*—Dawayne A Pinkney
(74) *Attorney, Agent, or Firm*—Robert Ambrose

(57) ABSTRACT

An adaptive optics system that allows a user to see an aberration-corrected image. The system includes a stimulus that is in optical connection with a user's eyes, a wavefront sensor that is in optical connection with the user's eyes, binocular convergence compensating adaptive optics hardware that is in optical connection with the stimulus and the user's eyes and is also electrically connected to the wavefront sensor, and a badal optometer that is in optical connection with the stimulus and the user's eyes and is in optical connection with the wavefront sensor and the user's eyes.

16 Claims, 1 Drawing Sheet

ADAPTIVE OPTIC OPHTHALMIC DESIGN SYSTEM

This application claims the benefit under 35 U.S.C. § 119(e) of U.S. provisional application Ser. No. 60/752,717 filed Dec. 21, 2005.

This invention is related to contact lenses. In particular, the present invention is related to customized design of presbyopic contact lenses

BACKGROUND

Contact lenses are widely used for correcting many different types of vision deficiencies. These include defects such as near-sightedness and far-sightedness (myopia and hypermetropia, respectively), astigmatic vision errors, and defects in near range vision usually associated with aging (presbyopia).

Current opinion holds that presbyopia occurs as a person ages when the lens of eye begins to crystallize and lose its elasticity, eventually resulting in the eye losing its accommodation—the ability to focus on nearby objects.

Some presbyopic persons have both near vision and far vision defects, requiring bifocal lenses to properly correct their vision. Many people prefer wearing contact lenses to correct their vision rather than bifocal or progressive spectacles. However, creating a bifocal or simultaneous vision lens for presbyopes entails finding the optimal visual "compromise" between near and far vision. The registration or location of the contact lens on the cornea, does not allow selection of the ADD zone as a function of gaze.

Testing refractive errors of the eye involves several tests, some of which are subjective, and others that are objective in nature. Objective refraction tests include the use of retinoscopy, phoropter systems, wavefront sensors and autorefractors. A phoropter can be manipulated by a control unit so that an operator's movement can be minimized during the testing procedure (see U.S. Pat. No. 4,861,156), and is expressly incorporated by reference as if fully set forth herein.

Wavefront sensors may also be used to detect refractive errors in the eye, such as for example, a Shack-Hartmann wavefront sensor. Measurements of the wavefront aberrations of the eye to a high degree of precision using an improved Hartmann-Shack wavefront sensor are described in U.S. Pat. No. 5,777,719, which is expressly incorporated by reference as if fully set forth herein. The wavefront sensor illuminates the retina with a narrow beam of light and then determines the refractive error of the eye, at all points in the pupil, by analysis of the outgoing wavefront scattered by the retina. Typically, this wavefront is fit to a basis set such as the Zernike index.

Objective refraction tests often to not correlate with subjective sphero-cylindrical correction or presbyopic correction. Furthermore, objective refractions are typically determined only at the distance conjugate in a monocular fashion. Differences in an eye's aberration, the individual's neural processing and visual requirements may limit the effectiveness of objective tests as vision is subjective. Subjective eye tests are more interactive than objective tests and may better encompass the entire visual system. The present invention seeks to correct the inadequacies of the prior art such as that included in adaptive optic phoropter systems by the inclusion of high spatial frequency adaptive optic technology, an optometer to vary the vergence of the visual stimulus and a binocular configuration to incorporate modified monovision into the lens designs. In the preferred embodiment of the present invention, the system has the ability to provide high spatial frequency aberration patterns, through focus, in a binocular fashion. As such, the system will simultaneously demonstrate the expected though focus vision to a subject and provide the information to calculate the customized lens designs

SUMMARY OF THE INVENTION

In accomplishing the foregoing, there is provided, in accordance with one aspect of the present invention an adaptive optics system that may include a stimulus that is in optical connections with a user's eye; a wavefront sensor that is in optical connection with the user's eye; adaptive optics hardware that is in optical connection with the stimulus and the users eye that is also electrically connected to the wavefront sensor. This system preferably allows the user to see an aberration-corrected image. In one embodiment of the present invention, the wavefront sensor may generate infrared light that is directed to the users eye and forms an optical path to and from the user's eye. In another embodiment of the present invention, the stimulus preferably generates visible light that forms an optical path to and from the user's eye. In another embodiment of the present invention the wavefront sensor is connected to the adaptive optics hardware in a closed-loop control configuration.

The present invention may also include a badal optometer, wherein the optometer provides distance compensation. In a related embodiment, the badal optometer may resolve vision to at least three distances: far, intermediate, and near vision. In this embodiment, the adaptive optics system provides aberration-corrected vision at each distance. In another embodiment, the user may input his preference for compromise vision.

The adaptive optics hardware of the present invention may include may be selected from the group consisting of MEMS devices and deformable mirrors.

The present invention also provides a method of providing an aberration-corrected image to a user that may include the steps of sensing the natural aberrations of the user's eye; correcting the natural aberrations of the user's eye using adaptive optics, and reflecting the aberration-corrected image to the user. In this method the sensing step may be performed by a wavefront sensor. In a related embodiment the correcting step is performed by one or more of the following: MEMs devices, flip-in mirrors, a beamsplitter, telecentric lenses and/or deformable mirrors.

In another embodiment of the present invention, a method for providing an optimal visual image to a subject may include the steps of exposing the subject to visible light generated by a stimulus; adapting the perceived distance of the stimulus with a badal optometer; directing infrared light from a wavefront sensor to the subject's eye; determining the aberrations in the users eye with a wavefront sensor; correcting the image of the stimulus according to the aberrations with an adaptive optics system; and providing said corrected image to said user. In this embodiment, the adaptive optics system may include MEMs technology connected to the wavefront sensor in a closed-loop configuration and the stimulus may be either white light or red/green light. In a related embodiment, a bandpass filter may be used to direct the paths of the visible and IR light paths.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Figure 1:
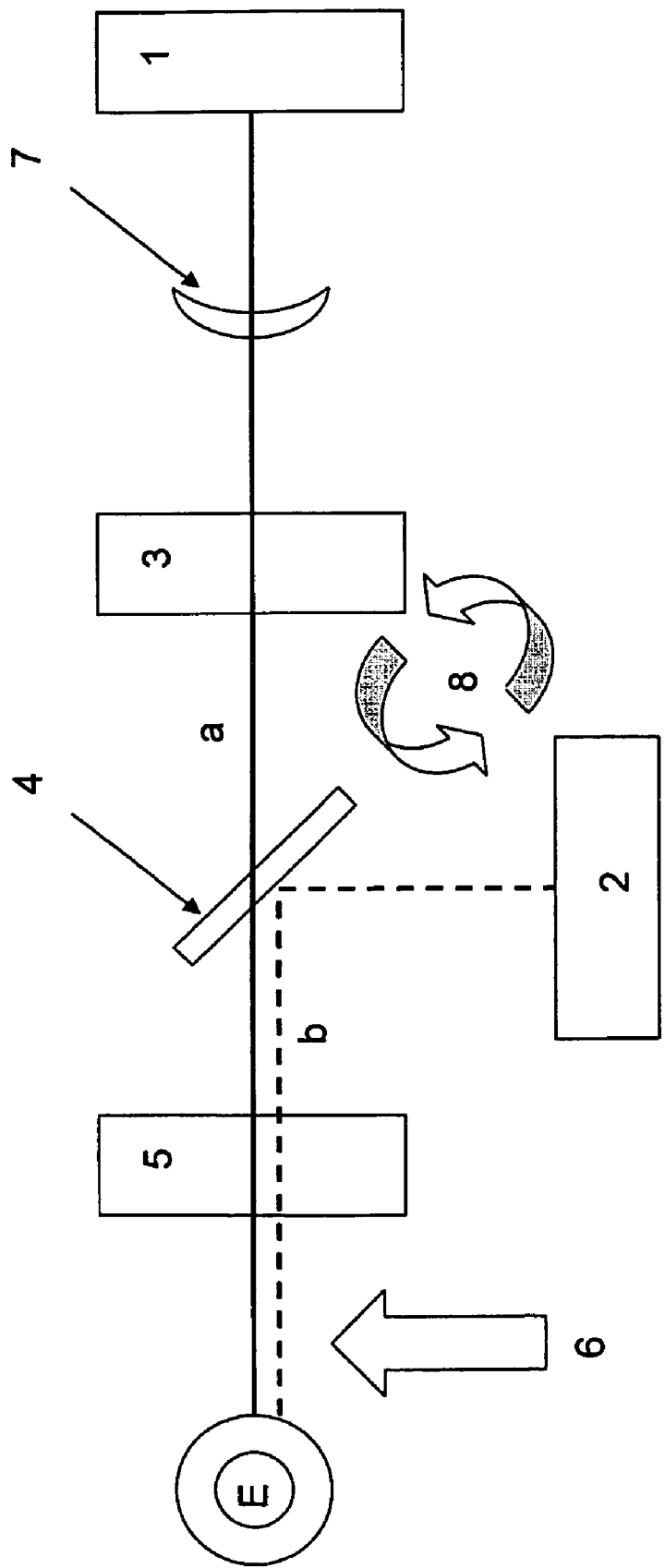
FIG. 1 FIG. 1 depicts the optical paths used in conjunction with one embodiment of the present invention.

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the manufacturing procedures are well known and commonly employed in the art. Conventional methods are used for these procedures, such as those provided in the art and various general references. Where a term is provided in the singular, the inventors also contemplate the plural of that term.

The present invention seeks to measure the aberrations of the eye and nearly simultaneously correct or manipulate the aberrations and allow the subject to subjectively assess vision and provide an objective measurement of the cumulative aberrations. Such a system may be particularly useful for subjects with presbyopia as it will enable a user to visualize the best through-focus compromise. Multiple axial measurement can be achieved through the present invention by combining a badal optometer that can approximate at least three vergences: distance vision (0 Diopters), intermediate vision (1 Diopter (typical)—vision used to view a computer screen) and near vision (2.5 Diopters (typical)—vision used to read) with high spatial frequency adaptive optics technology. In the preferred embodiment, the badal optometer can scan through a continuous range of vergence.

When a person "sees," light from an object is imaged onto the retina via the eye's refractive elements. Light is first refracted by the cornea, through the iris and then refracted by the crystalline lens. The crystalline lens acts as an auto-focusing element. The pupil is determined as the image of the iris. The retina changes the light (energy) into electric impulses that are carried through the optic nerve to the vision center (occipital cortex) of the brain where the image is interpreted.

Adaptive optics technology utilizes MEMS or deformable mirror technology. Adaptive optics compensates for optical aberrations by controlling the phase of the light waves, or wavefronts, incident on the retina—much like waves breaking on a shoreline. Non-uniformities in the refractive power of the eye blur the image on the retina. Typically, these aberrations increase with pupil diameter. A wavefront sensor accurately measures the aberrations of the eye to a higher degree than the sphero-cylindrical average of a standard phoropter. The stimulus of such a wavefront sensor is typically a beam from an infrared source, typically in the 850-nm range, which may be scattered by the retina. The wavefront sensor has the ability to measure the perturbated wavefront outgoing from the eye thus capturing the complete aberration profile of the eye's optics.

In one embodiment of the present invention, the apparatus of the present invention may include one or more of the following: a stimulus, a beam splitter, a band pass filter, a wavefront sensor, a computer capable of optical analyses (particularly closed-loop analyses), a high spatial resolution adaptive optical element, optical hardware to compensate for binocular convergence, a badal optometer and/or a means for user input.

An exemplary system is shown in FIG. 1. Referring to FIG. 1, there are two types of light according to the present invention, as shown by the two paths: visible light (a) and infrared light (b). Infrared light is preferably generated by a wavefront sensor (2) and preferably has a wavelength of approximately 850 nm. Visible light (a), as used in the present invention is preferably generated by a stimulus (1) and may be white or monochromatic light. Starting from the left side of FIG. 1, the user's eye (E) is pictured. Infrared light (b) from the wavefront sensor (2) forms one optical path to and from the user's eye (E). Visible light (a) generated by the stimulus (1) forms a second optical path to and from the user's eye (E).

Along the visible light optical path (a) from the user's eye (E) to the stimulus (1), there may be a badal optometer (5), a bandpass filter (4), and adaptive optics hardware (3). Along the infrared optical path (b) from the wavefront sensor (2) to the user's eye (E), there may be a bandpass filter (4) and a badal optometer (5). The bandpass filter (4) preferably allows the visible light (a) to pass through it to and from the user's eye (E) and the stimulus (1), while directing the infrared light (b) between the user's eye (E) and the wavefront sensor (2), preventing the infrared light (b) from traveling along the optical path between the bandpass filter (4) to the stimulus (1). The wavefront sensor (2), however, may have a closed-loop control system (8) between it and the adaptive optics hardware (3). The adaptive optics hardware (3) may include deformable mirrors and/or MEMS devices. The MEMS device will have stoke to change the curvature of the wavefront—not just the direction of the beam. The closed loop system (8) between the wavefront sensor (2) and the adaptive optics hardware (3) allows the wavefront sensor (2) to iterate until the adaptive optics hardware (3) changes such that it can project a substantially aberration-free image, or an image aberrated in a prescribed pattern, back to the user's eye (E).

The system may further optionally comprise a lens or lens system (7) along the optical path (a) from the user's eye (E) to the stimulus (1). The lens or lens system (7) may be convex or concave or a combination of both.

For example, in one embodiment of the present invention, infrared light (b) is directed towards the user's eye (E) and senses the natural aberrations of the user's eye and sends information to the wavefront sensor (2) in conjunction with a computer interface (not shown in FIG. 1). The wavefront sensor (2) measures the aberrations. This information is used by the computer to calculate the appropriate adjustment, by the adaptive optics system, to provide an aberration-corrected image. The wavefront sensor (2) determines the wavefront distortion as it passes through the user's eye's optics. A computer uses this information to create an internal, three-dimensional (3D) representation of the distorted wave. That 3D shape is then used to instruct adaptive optics hardware (3). In an embodiment in which MEMS devices are used, the MEMS actuators may move to positions that will minimize the distortion and "flatten" the wavefront or shape the wavefront in a prescribe fashion. This system provides both objective measurement of the aberrations and subjective feedback from the subject.

In a related embodiment, a user may be able to control their vision via the adaptive optic hardware (3) to manipulate the wavefront, i.e using a means (6) for the user to input his preference for the through-focus visual compromise. In a preferred embodiment, the means (6) may be a control device, such as a joystick to change the stimulus (1) or target to an image that appears clear. This process may iterate until the best target image is found.

In an embodiment in which the user is a presbyope, the system can be used to determine the optimal through-focus visual compromise. In a preferred embodiment, the system is binocular and can adjust for convergence as the vergence is modified by the badal optometer (5). The badal optometer (5) will adjust to multiple vergences as the adaptive optics hardware (3) manipulates the wavefront. In a more preferred embodiment, the wavefront will be adjusted to at least three vergences—far, intermediate and near.

The combined information of the user's subjective input and of the best through-focus cumulative aberration pattern finally allows to calculate a customized lens designs based on the optimal visual compromise for said user.

The invention has been described in detail, with particular reference to certain preferred embodiments, in order to enable the reader to practice the invention without undue experimentation. A person having ordinary skill in the art will readily recognize that many of the previous components, compositions, and/or parameters may be varied or modified to a reasonable extent without departing from the scope and spirit of the invention. Furthermore, titles, headings, example materials or the like are provided to enhance the reader's comprehension of this document, and should not be read as limiting the scope of the present invention. Accordingly, the invention is defined by the following claims, and reasonable extensions and equivalents thereof.

I claim:

1. An adaptive optics system comprising:
   a stimulus that is in optical connection with a user's eye;
   a wavefront sensor that is in optical connection with the user's eye;
   binocular convergence compensating adaptive optics hardware that is in optical connection with said stimulus and said user's eye and is also electrically connected to said wavefront sensor; and
   a badal optometer that is in optical connection with said stimulus and said user's eye and is in optical connection with said wavefront sensor and said user's eye;
   wherein said system allows said user to see an aberration-corrected image.

2. The system of claim 1, wherein said wavefront sensor generates infrared light that is directed to said user's eye and forms an optical path to and from said user's eye.

3. The system of claim 1, wherein said stimulus generates visible light that forms an optical path to and from said user's eye.

4. The system of claim 1, wherein said wavefront sensor is connected to said adaptive optics hardware in a closed-loop control configuration.

5. The system of claim 1, wherein said badal optometer provides distance compensation.

6. The system of claim 5, wherein said badal optometer resolves vision to at least three distances: far, intermediate, and near vision.

7. The system of claim 6, wherein said adaptive optics system provides aberration-corrected vision at each distance.

8. The system of claim 7, further comprising a means for the user to input his preference for compromise vision.

9. The system of claim 1 wherein said adaptive optics hardware may be selected from the group consisting of MEMS devices and deformable mirrors.

10. A method of providing an aberration-corrected image to a user comprising:
    sensing the natural aberrations of said user's eye with a wave front sensor;
    providing distance compensation to said user's eye with a badal optometer;
    correcting the natural aberrations of said user's eye using binocular convergence compensating adaptive optics, and
    reflecting said aberration-corrected image to said user.

11. The method of claim 10, wherein said correcting step is performed by one or more of the following: MEMs devices, flip-in mirrors, a beamsplitter, telecentric lenses and/or deformable mirrors.

12. A method of providing a through-focus visual compromise image to a subject comprising:
    exposing said subject to visible light generated by a stimulus;
    adapting the perceived distance of the stimulus with a badal optometer;
    directing infrared light from a wavefront sensor to a subject's eye;
    determining the aberrations in the users eye with a wavefront sensor;
    correcting the image of said stimulus according to said aberrations with a binocular convergence compensating adaptive optics system; and
    providing said corrected image to said user.

13. A method of providing an optimal visual image to a subject comprising:
    exposing said subject to visible light generated by a stimulus;
    adapting the perceived distance of the stimulus with a badal optometer;
    directing infrared light from a wavefront sensor to the subject's eye;
    determining the aberrations in the users eye with a wavefront sensor;
    correcting the image of said stimulus according to said aberrations with a binocular convergence compensating adaptive optics system; and
    providing said corrected image to said user.

14. The method of claim 13, wherein adaptive optics system further comprises MEMs technology connected to said wavefront sensor in a closed-loop configuration.

15. The method claim of 13, where said stimulus is selected from the group of white light and red/green light.

16. The method of claim 13, further comprising providing a bandpass filter to direct the paths of the visible and IR light paths.

* * * * *